United States Patent [19]

Atwood

[11] 4,321,127
[45] Mar. 23, 1982

[54] COAL LIQUEFACTION USING LIQUID CLATHRATES

[75] Inventor: Jerry L. Atwood, Tuscaloosa, Ala.

[73] Assignee: University of Alabama, University, Ala.

[21] Appl. No.: 240,903

[22] Filed: Mar. 5, 1981

Related U.S. Application Data

[63] Continuation of Ser. No. 138,997, Apr. 10, 1980, abandoned.

[51] Int. Cl.³ .................. C10G 1/00; C10G 21/12
[52] U.S. Cl. ..................... 208/8 LE; 208/11 LE; 208/322
[58] Field of Search ............... 208/8 LE, 11 LE, 322

[56] References Cited

U.S. PATENT DOCUMENTS 4,024,170  5/1977  Atwood .................. 208/322

*Primary Examiner*—Delbert E. Gantz
*Assistant Examiner*—William G. Wright
*Attorney, Agent, or Firm*—Oblon, Fisher, Spivak, McClelland & Maier

[57] ABSTRACT

The method for the liquefaction of a solid carbonaceous substance whereby the liquefaction takes place as a result of the addition of a liquid clathrate to said substance. The liquid clathrate layer then contains the liquified petroleum oil products which are then separated from the liquid clathrate.

26 Claims, No Drawings

COAL LIQUEFACTION USING LIQUID CLATHRATES

This is a continuation, of application Ser. No. 138,997, filed Apr. 10, 1980, now abandoned.

BACKGROUND OF THE INVENTION

1. Field of the Invention

The present invention relates to low temperature coal liquefaction, and more particularly to liquefaction of coal using a liquid clathrate.

2. Description of the Prior Art

The oldest of the modern direct liquefaction processes, dating back to about 1962, is the Solvent Refined Coal (SRC) process, developed by Spencer Chemical.

In the original process, now known as SRC-I, pulverized raw coal is mixed with a process-derived solvent and a small amount of hydrogen at high temperature and pressure. The coal dissolves; most of its ash and much of its sulfur settle out and can be removed by filtration. The resulting relatively clean liquid can be burned in that form, or it can be cooled to a tarlike solid for easier transportation and storage.

A later, modified version, SRC-II, uses more hydrogen and operates under more severe conditions of temperature, pressure, and residence time. Most of the coal is converted to liquids mainly naphtha and boiler fuel.

Recently, two 6000 ton-per-day demonstration plants—a modified SRC-I in Kentucky and an SRC-II in West Virginia—have been proposed. Conceivably, commercial-scale plants using either of these processes could be in operation by 1989 or 1990.

Another approach to coal dissolution is the Exxon Donor Solvent (EDS) process. Crushed, dried feed coal is slurried with a hydrogenated recycle solvent (the donor solvent) and fed, along with gaseous hydrogen into an upward plug-flow reactor of fairly simple design. The effluent is separated by distillation into several fractions: the recycle solvent, depleted of its hydrogen; light hydrocarbon gases; heavier distillates, boiling at up to 1000° F.; and a heavy vacuum bottoms stream containing still heavier liquids, unconverted coal, and ash.

The recycle solvent is rehydrogenated catalytically in a conventional fixed-bed reactor. Bottoms are fed with steam and air to an Exxon Flexi-coking unit, which produces additional liquids and low Btu gas. In contrast to the other processes, hydrogen is obtained by steam-forming the light hydrocarbon gases.

The third direct liquefaction process currently being seriously considered for commercialization is the H-Coal process, developed by Hydrocarbon Research Inc. The H-Coal process employs no solvent. Instead, dried, crushed coal is slurried with heavy distillate from the process, pressurized, mixed with compressed hydrogen, preheated and fed to an ebullated-bed catalytic reactor.

Effluent gases are cooled to separate heavier components as liquids. Light hydrocarbons, ammonia and hydrogen sulfide are absorbed from the remaining hydrogen-rich gas, which is recompressed and recycled to the input slurry. The liquid-solid portion, containing unconverted coal, ash and oil goes to a flash separator. The lighter portions go to an atmospheric distillation unit, while the bottoms are separated with a hydrocyclone, a liquid solid separator, and a vacuum still.

All of these direct liquefaction procedures require considerable energy input and are not truly cost effective techniques.

A need therefore exists for the development of a low-energy input liquefaction process.

SUMMARY OF THE INVENTION

Accordingly, it is one object of the present invention to provide a process for the liquefaction of coal at low temperatures with minimum input of energy.

It is another more particular object of the present invention to produce petroleum oil fractions from coal.

These and other objects of the invention, as will hereinafter become more readily apparent by the following description, have been attained by providing a method for the liquefaction of coal which comprises admixing said coal with a liquid clathrate, maintaining said admixture for a period sufficient to form a liquid clathrate layer containing liquified petroleum oil products, decomposing said clathrate to separate said clathrate from said petroleum oil, whereby a petroleum oil phase is produced, and separating said petroleum oil phase from said decomposition products.

DESCRIPTION OF THE PREFERRED EMBODIMENTS

According to the present invention, coal is liquified by admixing the coal with a liquid clathrate. The chemical mechanism for this phenomena is not fully known, but seems to have similarities to a solvent or catalytic effect. The really surprising aspect of this process is that it occurs at or near room temperature, and in any event, at temperatures which are very far below those temperatures for any other known liquefaction technique. For instance, liquifaction can be effected at temperatures of from 10°–80° C. and preferably 15° C.–50° C. In many cases, liquefaction will occur at or near room temperature with no application of heat.

The coal or solid carbonaceous material used in this process can be any form of coal including bituminous and subbituminous coal, lignite, or such coal-like forms as oil shale or tar sands. The one which was used predominantly in our research was bituminous which is mined locally at the Chetopa mine, Mary Lee Seam. The analysis of the coal used can vary widely from 40 to 80% by weight carbon, 3 to 15 percent by weight hydrogen, 0 to 10 percent by weight oxygen, 0 to 15 percent by weight nitrogen and 0 to 7 percent by weight sulfur. Preferred carbon ranges from 80–100 parts per 60–80 parts hydrogen, 0 to 8 parts oxygen, 0 to 8 parts nitrogen and 0 to 4 parts sulfur.

It is preferred to use very dry coal because many of the clathrates used herein are moisture sensitive. If necessary, the coal can be dried by conventional means to a dryness of 1 weight percent or less.

The coal may be used in rock form, as mined, or may be crushed to a size of 0.5 mm or smaller to increase the surface area to enable maximum contact with the liquid clathrate. It appears that the size of the coal used merely affects the period of time of liquid clathrate contact. Thus, the larger the coal formation, the longer will be the contact time necessary. The contact time can be reduced by applying mixing or gentle aggitation. Thus, the larger chunks of coal can be liquefied as fast as smaller particles if aggitation or stirring is applied during the contact time. It is believed to be possible in some instances to pump the liquid clathrate into a coal mine shaft whereby the coal liquefaction will occur in situ within the mine and thereafter to pump out a petroleum oil-like product directly from the shaft. If this will work, the commercial advantages are, of course readily apparent.

"Liquid Clathrate" is a term of art which refers to certain enclosure compounds. A liquid clathrate is a loose structure of a complex salt and an aromatic whereby the aromatic is entrapped into the complex. The aromatics can be retrieved unchanged by lowering the temperature. The liquid clathrate will only accomodate a certain number of aromatic molecules and the excess aromatic will be immiscible with the clathrate. See J. L. Atwood et al, Journal Organometallic Chemistry 66, 15-21 (1974) 42, C 77-79, (1972), 61. 43-48 (1973), 65, 145-154(1974).

In general, the clathrates used herein are any of those disclosed and claimed in U.S. Pat. No. 4,024,170 which disclose crown ether containing clathrates.

The liquid clathrates used herein may have the formula $$M(Q_n R_{3m} X) \cdot vY$$

wherein M is a mono, di- or trivalent cation, X is an anion of a mono-, di- or tri-negative salt, Q is Al or Ga, n is 2-4, v is 4 to 40 and Y is a hydrocarbon aromatic compound.

The cation M may be a multidentate macromolecular complex salt cation, hereafter referred to as "crown ether complex salt cation", or a simple salt cation. For instance, suitable simple salt cations include alkali, alkaline, quaternary ammonium, phosphonium, arsonium, sulfonium, tellurium or mixtures thereof, including $K+$, $Rb+$, $Cs+$, $Nr'_4+$, $Cr(C_6H_6)_2+$, $Co(C_5H_5)_2+$, $TlR'_2+$, $PR'_4+$, wherein R' is hydrogen, alkyl of $C_{1-10}$, phenyl or naphthyl. Alternatively, crown ether complex salt cations may be used, such as those of the formula

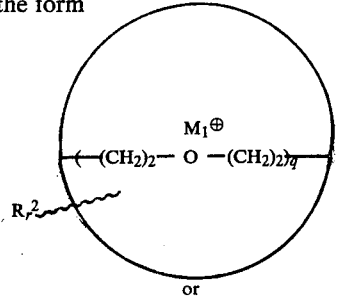

wherein q is 4-8 and $R^2$ is a lower alkyl, aryl or aryl which is fused to said ring, and r is an integer of 0-4. The complex can be formed wherein the metal cation $M_1 \oplus$ is complexed with one or more than one crown ether in the form -continued

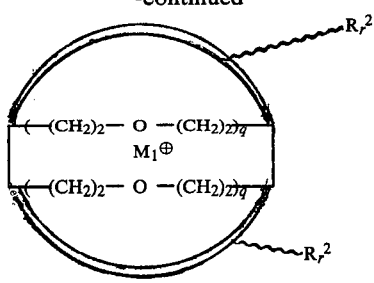

$M_1 \oplus$ in the above structure may be the same as M defined above, or may be a divalent cation such as $Ba^{++}$ or $Ca^{++}$ which when complexed with the crown ether is characterized by the said complex having the charge of the naked cation.

Particularly suitable crown ethers which can be used in the complexes include 18-crown-6, 15-crown-5 or dibenzo-18-crown-6, and those described in the said copending crown ether patent application.

It has been found that the larger the cation $M_1$, the greater will be the number of molecules of hydrocarbon aromatic compounds which can be entrapped by the complex salt.

Suitable hydrocarbon aromatic compounds which can be used in forming the clathrate include benzene, toluene, o-, m-, or p-xylene, mesitylene, tetramethylbenzene, dipropylbenzene, diisopropylbenzene, naphthalene, tetralin, anthracene or phenanthracene. Benzene and toluene have been demonstrated to give good results.

The anion X may be any mono-, di or tri-negative salt anion such as halide, particularly $Cl^-$, $F^-$, $Br^-$, or $I^-$, azide, $SCN^-$, $SeCN^-$, nitrite, nitrate, lower alkyl acyl such as $CH_3-COO^-$, or $HCOO^-$, hydroxide, carbonate, sulfate or phosphate.

R in the formula may be a lower alkyl of 1-8 carbon atoms, particularly methyl, ethyl, propyl or butyl when Q is Al, the $Al_n R_{3n}$ component is derived from an aluminum trialkyl compound such as trimethyl aluminum, triethyl aluminum, or the like. However, other aluminum alkyl compounds can be used such as tri-n-propyl aluminum, tri-isopropyl aluminum, or tri-n-butyl aluminum. When Q is Ga, the corresponding $Ga_n R_{3n}$ component is derived from the corresponding gallium containing compound.

In general, one must have a complex salt having the angular geometry

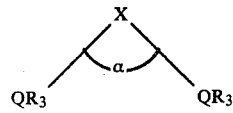

to form the aromatic clathrate; whereas a symetrical anionic structure

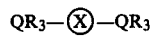

will not normally clathrate.

The nature of the clathrate interaction is thus related to the nature of the anion, the latice energy, size of the cation and the size of the aromatic molecule. It is expected that other clathrates based on systems other then the $QR_3$ or $GaR_3$ models as discussed above, will be useable. For instance, liquid clathrates of the form K[CH₃Se{Al(CH₃)₃{₃}].6C₆H₆ can be used herein.

Further information concerning liquid clathrates can be obtained by reference to Atwood "Liquid Clathrates," *Recent Developments in Separation Sciences*, CRC Press, Cleveland, 1977, pages 195–209 (1978).

Mixtures of different clathrates can be used in the admixture to liquify the coal.

The complex salt used however, can be prepared by reacting the aluminum alkyl compound with a simple salt such as the alkali nitrate carbonate, sulfate, azide or the like. Upon introduction of the hydrocarbon aromatic compound, the salt is converted into the liquid clathrate. The liquid clathrate can be produced in one step or in multiple steps. Thus, the simple salt, the aluminum alkyl and the aromatic, such as benzene or toluene, can be admixed together in one step, or the simple salt and the aromatic can be admixed and then combined with coal and aluminum alkyl to form the clathrate in situ with the coal. The former is the method of preference. Any such combination is suitable for forming the clathrate.

The clathrate forming reaction can occur at room temperature or higher, up to about 190° C., depending on the particular choice of materials. Beyond 190° C., the aluminum alkyl will decompose. Good results are attainable in the range of 15°–80° C. Upon cooling, a temperature will be reached at which the clathrate will decompose back to the complex salt and the aromatic compound. The only limitation on the contact conditions between the clathrate and the coal seems to be that the temperature must be selected such that the liquid clathrate will be in existence during the period of contact. If one is concerned with materials which will clathrate at a temperature of say. 60° C. but wherein the clathrate decomposes back to the complex salt below that temperature, of course, the temperature of coal-clathrate contact must be above 60° C.

When the crown ether complex salt is used, the crown ether, simple salt, aluminum alkyl and aromatic must all be brought together. The order of addition does not seem to be critical. In fact, the complex salt can first be formed, converted into a clathrate, and then admixed with the crown ether, whereupon the new ether containing complex will clathrate with additional aromatic compound, as compared to the quantity clathrated by the non-crown ether complex salt.

If the liquid clathrate is formed in an excess of the aromatic, which is usually the case, the existence of the clathrate can be visually detected by a phase separation between a top aromatic hydrocarbon compound solvent layer and the bottom liquid clathrate.

When the clathrate is admixed with the coal, the clathrate is immediately discolored by a black petroleum-like product. Thereafter, the aromatic solvent layer gradually becomes discolored as the lighter liquified petroleum products are leached into that layer. The light oil dissolved in the solvent accounts for 5–10% of the oil recovery. From 250 parts to 2500 parts or more of liquid clathrate per part by weight of coal is sufficient to obtain the desired effect.

Petroleum oil separation is attainable almost immediately, with useable yields appearing after 30 minutes. Contact, however, can be maintained for an indefinite period of time and often 1–2 days is desirable.

At the termination of the contact period, the aromatic solvent layer can be decanted off and the hydrocarbon oils contained therein recovered by ordinary separation means. If the contact time has been permitted for a sufficiently long period, most of the petroleum like oil will have been either solvent extracted into that solvent phase or, in particular, the heavier oils, will have been precipitated out at the bottom of the container. Alternatively, the temperature of the clathrate is reduced or the mixture is subjected to distillation in order to decompose the clathrate and to crystallize out the complex salt. A petroleum oil phase and a solvent (aromatic hydrocarbon) phase above it will appear upon the decomposition of the clathrate. As asphalt-like material is found to cover the complex salt crystals, which asphalt has been found to have an average molecular weight of 300–400 and a pour point above 200° C. The fact that the residue is an asphalt-like material evidences that the coal is being chemically modified in some manner although the precise mechanism for this modification is as yet unknown. The ability of the clathrate to be discolored rapidly after contact with the coal is evidence of a solvent type activity. On the other hand, the fact that the structure of the residue seems to be altered and the fact that no discernable amounts of the complex salt used to make the clathrate is lost, leads to a catalysis explanation.

Instead of decomposing the clathrate by reduction in temperature, where the clathrate selected is water or oxygen sensitive, it can alternatively be decomposed by introduction of water moisture or oxygen into the system which attacks the aluminum alkyl component of the salt. For this reason, it is desirable to carry out the coal-clathrate contact in a dry, inert atmosphere. A blanket of nitrogen, argon or other inert gas can be desirably maintained over the mixture during the period of contact.

The petroleum oil layer formed after the decomposition of the clathrate, is then collected. Tests of the oil confirm that it is a petroleum oil having a weight average molecular weight of from 40 to 300 and a boiling point of from 30° to 300° C. Spectroscopic analysis has confirmed that the oil being produced is a hydrocarbon oil containing a multiplicity of different hydrocarbon products. In the 110° C. boiling fraction, more than seventy different compounds result. The present inventor expects that the limitation in the yield of petroleum oil produced is a function of the amount of hydrogen present in the coal sample. Oil recovery amounts to about 10–15% by weight based on the weight of bituminous coal treated. Much higher yields have been obtained for lignite and for tar sands. Good results have been attained with clathrates of the form:

K[Al₂Me₆N₃]

NMe₄[Al₂Me₆Cl]

NMe₄[Al₂Me₆I]

NEt₄[Al₂Me₆I]

NPr₄[Al₂Me₆I]

NEt₄[Al₂Me₆NO₃]

NEt₄[Al₂Et₆NO₃]

K₂[Al₂Me₆SO₄]

The economics of the present technique for coal liquefaction are extremely attractive. Unlike all other known liquefaction procedures, little or no heat input is required. Moreover, the cost of producing the clathrates is very modest and the loss factor of the complex salts used to produce the clathrates is small.

Having now generally described the invention, a more complete understanding can be attained by reference to certain specific examples which are provided herein for purposes of illustration only and are not intended to be construed as limiting the invention unless otherwise specifically claimed as such.

EXAMPLE 1

Preparation of Liquid Clathrates

The two different ways in which liquid clathrates may be prepared are best illustrated by reference to the $K[Al_2(CH_3)_6N_3]$ complex. 0.010 mol $Al(CH_3)_3$ was added to 0.005 mol $KN_3$ in an $N_2$ atmosphere dry box. The mixture was sealed in a Eisoher-Porter tube, removed from the dry box, heated, returned to the dry box, and opened. Another 0.005 mol $Al(CH_3)_3$ was then added to the powdered contents. After three cycles of grinding, adding $Al(CH_3)_3$, and heating the white crystalline product was dried under vacuum. Addition of benzene (~0.10 mol), followed by heating at 60° C. for 1 hour afforded the liquid clathrate $K[Al_2(CH_3)_6N_3]\cdot 5.8\ C_6H_6$.

Another method for production of the clathrates involves simply the addition of 0.005 mol $KN_3$ and 0.010 mol $(Al(CH_3)_3$ to ~0.10 mol $C_6H_6$ in the dry box. The liquid clathrate identical in composition to the one prepared by the previous method was obtained in 1 hour. All the following liquid clathrates were synthesized in this fashion.

| Compound | Aromatic | Maximum A/A ratio |
|---|---|---|
| $K[Al_2(CH_3)_6N_3]$ | benzene | 5.8 |
| $Rb[Al_2(CH_3)_6N_3]$ | benzene | 6.1 |
| $Cs[Al_2(CH_3)_6N_3]$ | benzene | 7.4 |
| $K[Al_2(CH_3)_6NO_3]$ | benzene | 7.0 |
| $Cs[Al_2(CH_3)_6NO_3]$ | benzene | 12.0 |
| $[N(C_2H_5)_4][Al_2(CH_3)_6NO_3]$ | benzene | 9.8 |
| $[N(CH_3)_4][Al_2(CH_3)_6Cl]$ | benzene | 8.1 |
| $[N(CH_3)_4][Al_3CH_3)_6I]$ | benzene | 6.5 |
| $[N(C_2H_5)_4][Al_2(CH_3)_6I]$ | benzene | 7.3 |
| $[N(C_3H_7)_4][Al_2(CH_3)_6I]$ | benzene | 9.0 |
| $[N(C_4H_9)_4][Al_2(CH_3)_6I]$ | benzene | 9.9 |
| $[N(C_5H_{11})_4][Al_2(CH_3)_6I]$ | benzene | 13.0 |
| $[P(C_3H_5)_4][Al_2(CH_3)_6I]$ | benzene | 16.1 |
| $[N(CH_3)_4][Al_2(CH_3)_6CH_3COO]$ | benzene | 6.3 |
| $Rb[Al_2(C_3H_5)_6N_3]$ | benzene | 3.8 |
| $[N(CH_3)_4][Al_2(C_2H_5)_6I]$ | benzene | 18.7 |
| $[N(C_2H_5)_4][Al_2(C_2H_5)_6I]$ | benzene | 15.9 |
| $[N(C_3H_7)_4][Al_2(C_2H_5)_6I]$ | benzene | 17.1 |
| $[N(C_4H_9)_4][Al_2(C_2H_4)_6I]$ | benzene | 18.0 |
| $[N(C_5H_{11})_4][Al_2(C_2H_5)_6I]$ | benzene | 20.4 |
| $[N(C_6H_{13})_4][Al_2(C_2H_5)_6I]$ | benzene | 34.4 |
| $[N(C_2H_5)_4][Al_2(C_3H_7)_6I]$ | benzene | 19.0 |
| $[N(C_3H_7)_4][Al_2(C_3H_7)_6I]$ | benzene | 22.6 |
| $[N(C_5H_{11})_4][Al_2(C_3H_7)_6I]$ | benzene | 42.2 |
| $[N(CH_3)_4][Al_2(C_4H_9)_6F]$ | benzene | 18.0 |
| $K[Al_2(CH_3)_6SCN]$ | toluene | 2.5 |
| $K[Al_2(CH_3)_6N_3]$ | toluene | 3.8 |
| $Rb[Al_2(CH_3)_6N_3]$ | toluene | 5.7 |
| $Cs[Al_2(CH_3)_6N_3]$ | toluene | 6.3 |
| $[N(C_2H_5)_4][Al_2(CH_3)_6NO_3]$ | toluene | 6.2 |
| $[N(CH_3)_4][Al_2(CH_3)_4I]$ | toluene | 2.9 |
| $[N(CH_3)_4][Al_2(CH_3)_6Cl]$ | toluene | 5.6 |
| $[N(CH_3)_4][Al_2(CH_3)_6Br]$ | toluene | 5.5 |
| $[N(CH_3)_4][Al_2(CH_3)_6I]$ | toluene | 5.0 |
| $[N(C_2H_5)_4][Al_2(CH_3)_6I]$ | toluene | 6.0 |
| $[N(C_3H_7)_4][Al_2(CH_3)_6I]$ | toluene | 6.4 |
| $[N(C_4H_9)_4][Al_2(CH_3)_6Br]$ | toluene | 9.3 |
| $[N(C_4H_9)_4][Al_2(CH_3)_6I]$ | toluene | 7.0 |
| $[N(C_5H_{11})_4][Al_2(CH_3)_6I]$ | toluene | 11.0 |
| $[N(C_6H_5)(CH_3)_3][Al_2(CH_3)_6I]$ | toluene | 8.4 |
| $[N(CH_3)_4][Al_2(C_2H_5)_6I]$ | toluene | 12.9 |
| $[N(C_2H_5)_4][Al_2(C_2H_5)_6I]$ | toluene | 10.6 |
| $[N(C_3H_7)_4][Al_2(C_2H_5)_6I]$ | toluene | 11.1 |
| $[N(C_4H_7)_4][Al_2(C_2H_5)_6I]$ | toluene | 13.5 |
| $[N(C_5H_{11})_4][Al_2(C_2H_5)_6I]$ | toluene | 18.4 |
| $[N(C_6H_{13})_4][Al_2(C_2H_5)_6I]$ | toluene | 30.2 |
| $[N(C_2H_5)_4][Al_2(C_3H_7)_6NO_3]$ | toluene | 14.8 |
| $[N(C_3H_7)_4][Al_2(C_3H_7)_6I]$ | toluene | 24.7 |
| $[N(C_2H_5)_4][Al_2(CH_3)_6I]$ | ethylbenzene | 4.6 |
| $[N(C_3H_7)_4][Al_2(CH_3)_6I]$ | ethylbenzene | 5.0 |
| $[N(C_4H_9)_4][Al_2(CH_3)_6I]$ | ethylbenzene | 5.9 |
| $[N(C_5H_{11})_4][Al_2(CH_3)_6I]$ | ethylbenzene | 11.0 |
| $[N(CH_3)_4][Al_2(CH_3)_6F]$ | ethylbenzene | 2.4 |
| $[N(CH_3)_4][Al_2(C_2H_5)_6I]$ | ethylbenzene | 10.6 |
| $[N(C_2H_5)_4][Al_2(C_2H_5)_6I]$ | ethylbenzene | 8.6 |
| $[N(C_3H_7)_4][Al_2(C_2H_5)_6I]$ | ethylbenzene | 9.1 |
| $[N(C_4H_9)_4][Al_2(C_2H_5)_6I]$ | ethylbenzene | 9.7 |
| $[N(C_5H_{11})_4][Al_2(C_2H_5)_6I]$ | ethylbenzene | 13.2 |
| $[N(C_6H_{13})_4][Al_2(C_2H_5)_6I]$ | ethylbenzene | 15.8 |
| $[N(C_7H_{15})_4][Al_2(C_2H_5)_6I]$ | ethylbenzene | 17.4 |
| $[N(C_3H_7)_4][Al_2(C_3H_7)_6I]$ | ethylbenzene | 17.3 |
| $[N(CH_3)_4][Al_2(C_2H_5)_6I]$ | propylbenzene | 8.0 |
| $[N(C_3H_7)_4][Al_2(C_2H_5)_6I]$ | propylbenzene | 7.2 |
| $[N(C_5H_{11})_4][Al_2(C_2H_5)_6I]$ | propylbenzene | 10.2 |
| $[N(CH_3)_4][Al_2(C_2H_5)_6I]$ | O-xylene | 12.9 |
| $[N(C_2H_5)_4][Al_2(C_2H_5)_6I]$ | O-xylene | 11.8 |
| $[N(C_3H_7)_4][Al_2(C_2H_5)_6I]$ | o-xylene | 11.3 |
| $[N(C_4H_9)_4][Al_2(C_2H_5)_6I]$ | o-xylene | 12.5 |
| $[N(C_5H_{11})_4][Al_2(C_2H_5)_6I]$ | o-xylene | 21.5 |
| $[N(C_6H_{13})_4][Al_2(C_2H_5)_6I]$ | o-xylene | 39.6 |
| $[N(C_5H_{11})_4][Al_2(CH_3)_6I]$ | m-xylene | 6.0 |
| $[N(CH_3)_4][Al_2(CH_3)_6F]$ | m-xylene | 3.1 |
| $[N(CH_3)_4][Al_2(C_2H_5)_6I]$ | m-xylene | 9.1 |
| $[N(C_2H_5)_4][Al_2(C_2H_5)_6I]$ | m-xylene | 7.6 |
| $[N(C_3H_7)_4][Al_2(C_2H_5)_6I]$ | m-xylene | 6.0 |
| $[N(C_4H_9)_4][Al_2(C_2H_5)_6I]$ | m-xylene | 6.8 |
| $[N(C_5H_{11})_4][Al_2(C_2H_5)_6I]$ | m-xylene | 9.2 |
| $[N(C_6H_{13})_4][Al_2(C_2H_5)_6I]$ | m-xylene | 14.1 |
| $[N(C_3H_7)_4][Al_2(C_3H_7)_6I]$ | m-xylene | 16.3 |
| $Cs[Al_2(CH_3)_6N_3]$ | p-xylene | 4.3 |
| $[N(CH_3)_4][Al_2(CH_3)_6F]$ | p-zylene | 2.4 |
| $[N(C_5H_{11})_4][Al_2(CH_3)_6I]$ | p-xylene | 7.0 |
| $[N(CH_3)_4][Al_2(C_2H_5)_6I]$ | p-xylene | 9.2 |
| $[N(C_2H_5)_4][Al_2(C_2H_5)_6I]$ | p-xylene | 7.8 |
| $[N(C_3H_7)_4][Al_2(C_2H_5)_6I]$ | p-xylene | 8.5 |
| $[N(C_4H_9)_4][Al_2(C_2H_5)_6I]$ | p-xylene | 10.9 |
| $[N(C_5H_{11})_4][Al_2(C_2H_5)_6I]$ | p-xylene | 12.8 |
| $[N(C_6H_{13})_4][Al_2(C_2H_5)_6I]$ | p-xylene | 14.8 |
| $[N(C_3H_7)_4][Al_2(C_3H_7)_6I]$ | p-xylene | 13.6 |
| $[N(CH_3)_4][Al_2(CH_3)_6F]$ | mesitylene | 1.5 |
| $[N(C_5H_{11})_4][Al_2(CH_3)_6I]$ | mesitylene | 3.7 |
| $[N(CH_3)_4][Al_2(C_2H_5)_6I]$ | mesitylene | 7.5 |
| $[N(C_2H_5)_4][Al_2(C_2H_5)_6I]$ | mesitylene | 6.1 |
| $[N(C_3H_7)_4][Al_2(C_2H_5)_6I]$ | mesitylene | 5.2 |
| $[N(C_3H_7)_4][Al_2(C_3H_7)_6I]$ | mesitylene | 7.8 |
| $[N(C_5H_{11})_4][Al_2(C_3H_7)_6I]$ | mesitylene | 10.3 |
| $[N(CH_3)_4][Al_2(CH_3)_6F]$ | 1,2,3,5-tetramethylbenzene | 1.3 |

As the reaction proceeds, a separation of two liquid layers (liquid clathrate and excess aromatic) becomes obvious; the layers appear upon shaking just as oil and water.

Once a liquid clathrate has reached its maximum composition, it is not possible to cause a further uptake of aromatic molecules. The formulation of $K[Al_2(CH_3)_6N_3]\cdot 5.8\ C_6H_6$ in the above Table represents a maximum aromatic: anion ratio.

Analysis of the liquid clathrates was done by the integration of NMR spectra recorded on a Perkin-Elmer[R] R20-B spectrometer. The aromatic stoichiometries quoted in the Table are in each case the average of three preparations and integrations. A realistic standard deviation for them would be ±0.2 molecules.

The liquid clathrates, although water and oxygen sensitive, are much less reactive than the pure parent organometallic compounds.

EXAMPLE 2

Bituminous coal (Chetopa Mine, Mary Lee seam) was crushed to 1 mm diameter or less and dried at 100° C. for 24 hours. One hundred ml of liquid clathrate $[N(C_3H_7)_4][Al_2Me_6I]$. toluene) was contacted with 10 g of coal. Immediately 0.4 g dissolved. After heating at 80° C. for 12 hours, 1.9 g of coal was extracted or dissolved. Three products resulted: (1) light oil, 0.4 g, toluene-soluble; (2) heavy oil, 0.9 g, toluene-insoluble; (3) asphalt-like residue mixed with unreacted coal. The total amount of material extracted from the coal was 14% by weight.

EXAMPLE 2

The experiment of Example 2 wherein the liquid clathrate-coal solution was not heated above room temperature, but the contact time was 48 hours. 1.2 g of coal was extracted or dissolved. The product distribution was 0.3 g light oil and 0.5 g heavy oil.

EXAMPLE 4

The coal of Example 2 was added to 100 ml of $K[Al_2Me_{6n}]$.4.0 toluene, and the mixture was heated to 60° for 4 days. 2.2 g of coal was extracted or dissolved. The product distribution was 0.5 g light oil and 0.9 g heavy oil.

EXAMPLE 5

High sulfur (3% by weight S) subbituminous coal (Walker Co., AL) was crushed to 1 mm diameter or less and dried at 110° C. for 24 hours. One hundred ml of liquid clathrate ($[N(C_3H_7)_4][Al_2Me_6I]$. toluene) was contacted with 10 g of the coal. Immediately, 0.5 g dissolved. After heating to 60° C. for 6 hours, 0.6 g of light oil was obtained. (This was measured as the total weight gain in the toluene layer of the two phase system.

EXAMPLE 6

Lignite (East-Central AL) was dried at 110° C. for 4 days. (The weight loss was considerable, and it is estimated that 30% of the "ore" was water.) One hundred ml of liquid clathrate ($[NEt_4][Al_2Et_6I]$. benzene) was contacted with 10 g of the dried lignite. Immediately 0.5 g dissolved. After 4 hours at room temperature, 1.0 g of light oil resulted.

EXAMPLE 7

Tar sand (North Alabama), 10 g, was added to 100 ml of $[NEt_4][Al_2Me_6NO_3]$. toluene. After 1 hour, the excess toluene layer was darker in color than the liquid clathrate layer itself. 1.8 g of light oil was extracted. This was approximately 40% by weight of the organic material.

EXAMPLE 8

The coal of Example 2 was added to 100 ml of [K(18-crown-6)][$Al_2Me_6N_3$]. toluene, and the mixture was shaken vigorously for 1 hour. 0.3 g of light oil resulted.

What is intended to be claimed by Letters Patent is:

1. A method for the liquefaction of solid carbonaceous material which comprises admixing said solid carbonaceous material with a liquid clathrate, maintaining said admixture for a period sufficient to form a liquid clathrate layer containing liquified petroleum oil products, separating said petroleum oil from said clathrate.

2. The method for the liquefaction of coal of claim 1, wherein said coal is admixed with a liquid clathrate of the formula:

$$M(Q_nR_{3n}X).vY$$

wherein M is a uni-, di- or tri-positive cation, R is lower alkyl of 1-8 carbon atoms, X is an anion of a mono-, di-, or tri-negative salt wherein Q is Al or Ga, n is an integer of 2 to 4 and Y is an aromatic hydrocarbon compound and v is a number of 4 to 40.

3. The method for the liquefaction of coal, of claim 2, wherein said cation M is a crown ether complex salt cation of the formula M(crown ether).

4. The method for the liquefaction of coal of claim 1, wherein Q is Al.

5. The method for the liquefaction of coal of claim 2, wherein said cation M is a cation of a simple salt.

6. The method for the liquefaction of coal of Claim 3, 4 or 5 wherein M is an alkali metal ion, an alkaline earth metal ion, a quaternary ammoniun ion, phosphonium ion, arsonium ion, sulfonium ion, or telluronium ion.

7. The method for the liquefaction of coal of claim 6, wherein said cation is selected from the group consisting of $K^+$, $Rb^+$, $Cs^+$, $NR_4^+$, $PR'_4^+$, $Cr(C_6H_6)_2^+$, $TlR'_2^+$ wherein R' is hydrogen, an alkyl group of $C_1$-$C_{10}$ a phenyl or naphthyl.

8. The method for the liquefaction of coal of claim 1, wherein said admixture of coal and liquid clathrate is effected at a temperature of from 10° C. to 80° C.

9. The method of claim 6, wherein said admixture of coal and liquid clathrate is effected at a temperature of from 15° C.–50° C.

10. The method of claim 9, wherein said admixture of coal and liquid clathrate is effected at room temperature.

11. The method of claim 1, wherein said petroleum oil product is separated from said clathrate by decomposing said clathrate and recovering said oil therefrom.

12. The method for the liquefaction of coal of claim 2, wherein said anion is halide, azide, $SCN^-$, $SeCN^-$, nitrate, nitrite, lower alkyl, aryl, hydroxide, carbonate, sulfate, or phosphate.

13. The method for the liquefaction of coal of claim 2, wherein R is selected from the group consisting of methyl, ethyl, propyl and butyl and n=2.

14. The method for the liquefaction of coal of claim 2, wherein said aromatic hydrocarbon compound is benzene, toluene, o-, m- or p-xylene, mesitylene, tetramethylbenzene, ethylbenzene, dimethylbenzene, cumene, trimethylbenzene, dipropylbenzene, diisopropylbenzene, naphthalene, tetralin, anthracene or phenanthrene.

15. The method for the liquefaction of coal of claim 8, wherein said admixture of coal and liquid clathrate is maintained for a period of at least 30 minutes.

16. The method for the liquefaction of coal of claim 15, wherein said admixture is maintained for 6 hours at a temperature of 30°–50° C. and thereafter the temperature of said admixture is reduced to 10°–25° C. to effect decomposition of said clathrate.

17. The method for the liquefaction of coal of claim 1, wherein the coal used in the process has an analysis of 40 to 80 wt.% C, 3 to 15 wt.% H, 0 to 15 wt.% N, 0 to 10 wt.% O, and 0 to 7 wt.% S.

18. The method for the liquefaction of coal of claim 17, wherein the coal used in the process has an analysis of C 80–100, H 60–80, O 0–10, N 0–12, S 0–7.

19. The method for the liquefaction of solid carbonaceous material, of claim 1, wherein said solid carbonaceous material is selected from the group consisting of bituminous and subbituminous coal, lignite, tar sands, and oil shale.

20. The method of claim 19, wherein said coal is bituminous.

21. The method for the liquefaction of coal of claim 2, wherein said liquid clathrate is an admixture of different clathrates.

22. The method of claim 3, wherein said crown ether has the formula:

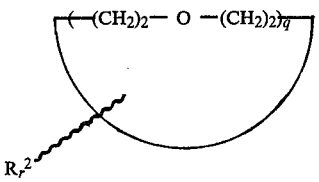

wherein q is 4–8 and $R^2$ is a lower alkyl, aryl or amyl fused to said ring and r is 0–4.

23. The method of claim 22, wherein said cation, M (crown ether)$^+$, has the form of

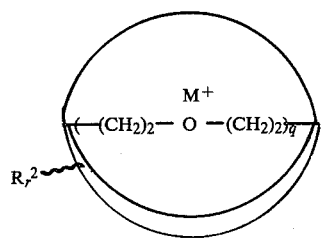

24. The method of claim 22, wherein said cation M (crown ether)$^+$ has the formula

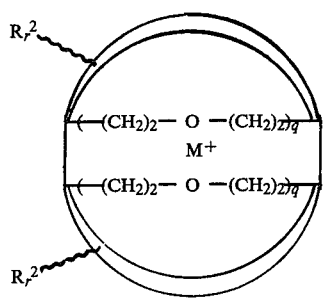

25. The method for the liquefaction of coal of claim 1, wherein from 250 to 2500 parts of liquid clathrate is admixed per 1 part of coal by weight.

26. The method for the liquefaction of coal of claim 1, wherein said petroleum oil product has a light average molecular weight of from 40 to 300 and a boiling point of from 30° to 250° C.

* * * * *